US00PP10794P

United States Patent [19]

Hedger

[11] Patent Number: Plant 10,794

[45] Date of Patent: Feb. 16, 1999

[54] CISTUS PLANT VARIETY NAMED 'HEDSO'

[75] Inventor: John Hedger, Pulborough, England

[73] Assignee: Pride of Place Plants, Inc., Sidney, Canada

[21] Appl. No.: 927,557

[22] Filed: Sep. 9, 1997

[51] Int. Cl.[6] ..... A01H 5/00

[52] U.S. Cl. ..... Plt./68.1

[58] Field of Search ..... Plt./68.1

*Primary Examiner*—Elizabeth Kemmerer
*Attorney, Agent, or Firm*—Christie, Parker & Hale, LLP

[57] ABSTRACT

A Cistus plant variety having variegated foliage.

1 Drawing Sheet

BACKGROUND OF THE INVENTION

The present invention relates to a new and distinct variety of Cistus which was discovered as a natural mutation in a controlled planting of the variety Cistus 'Peggy Sammons'. The varietal denomination of this new plant is 'Hedso'.

SUMMARY OF THE INVENTION

Among the novel characteristics possessed by the new variety which distinguish it from its parent and all other varieties of which I am aware are its attractive sage green foliage with a yellow marginal variegation and abundant display of large flowers in late spring in West Sussex, England.

Asexual reproduction by vegetative cuttings of the new variety as performed in West Sussex, England, shows that the foregoing and other distinguishing characteristics come true to form and are established and transmitted through succeeding progagations. Other known forms of asexual reproduction may be also used.

COMPARISON WITH PARENT

The parent of the variety, 'Peggy Sammons', has grey-green foliage with no variegation.

BRIEF DESCRIPTION OF ILLUSTRATION

The accompanying illustration shows a typical specimen of the vegetative growth and flowers of the new variety depicted in color as nearly true as it is reasonably possible to make the same in a color illustration of this character.

DESCRIPTION OF THE NEW VARIETY

Parentage: Mutation.
Parent: Cistus 'Peggy Sammons'.
Class: Cistus.

The following is a detailed description of the new variety, from specimens grown under glass in West Sussex, England in the month of April. The color terminology used is in accordance with The Royal Horticultural Society Colour Chart (RHSCC), and refers to plate numbers in the aforementioned color chart. Phenotypic expression may vary depending on light, environmental and cultural conditions.

Flower

Blooming habit: Blooms in late Spring in West Sussex, England.

A. Bud:
- (1) *Size.*—Short, small.

- (2) *Form.*—Ovate.
- (3) *Color.*—When sepals first divide, bud color is yellow.
- (4) *Sepals.*—Longer than bud, sepals spread when bloom opens.
- (5) *Peduncle.*—Length: Short. Aspect: Smooth. Strength: Erect, sturdy. Color: Near 138C.

Flower:
- (1) *Size.*—Average size when fully expanded — medium.
- (2) *Borne.*—Singly.
- (3) *Form.*—Round.
- (4) *Petalage.*—Number of petals under normal conditions — about 5. .
- (5) *Color.*—Near 54C to 55B with near white center. General tonality from a distance: Pink.

Petals:
- (1) *Texture.*—Soft.
- (2) *Appearance.*—Matte inside and outside.
- (3) *Form.*—Fan shape.

Reproductive Organs

A. Stamens:
- (1) *Arrangement.*—Regularly arranged around styles.
- (2) *Anthers.*—Deep yellow to gold.
- (3) *Filaments.*—Yellow.
- (4) *Pollen.*—Orange.

B. Pistils:
- (1) *Styles.*—Bunched, thin, medium length.
- (2) *Stigmas.*—Cream.

C. Characteristics of hips: Globular, medium size, cream color, seeds do not protrude.

Plant

A. Form: Compact.

B. Growth: Medium vigor and uniform branching. Attains height of about one meter.

C. Foliage:
- (1) *Size.*—Medium, about 45 mm long.
- (2) *Quantity.*—Abundant, single simple leaves.
- (3) *Color.*—Near 138A to 138B with yellow edge (margin) variegation, near 12B to 12C; of varying thickness.
- (4) *Shape.*—Ellipitic.
- (5) *Texture.*—Upper side downey; under side downey and hairy.
- (6) *Edge.*—Smooth.
- (7) *Veination.*—Pronounced.
- (8) *Rachis.*—Smooth.

(9) *Petioles.*—Top green/yellow/white; under side sage green.

(10) *Resistance to disease.*—Not known to be susceptible to any particular disease.

D. Wood:

(1) *New shoots.*—Silver grey green, bark smooth.

(2) *Old wood.*—Beige/brown; bark rough.

E. Flower stem: About 15 cm average from last cut (including peduncle).

G. Winter hardiness: Needs protection in all but warmest zones.

I claim:

1. A new and distinct Cistus plant variety, substantially as shown and described.

* * * * *

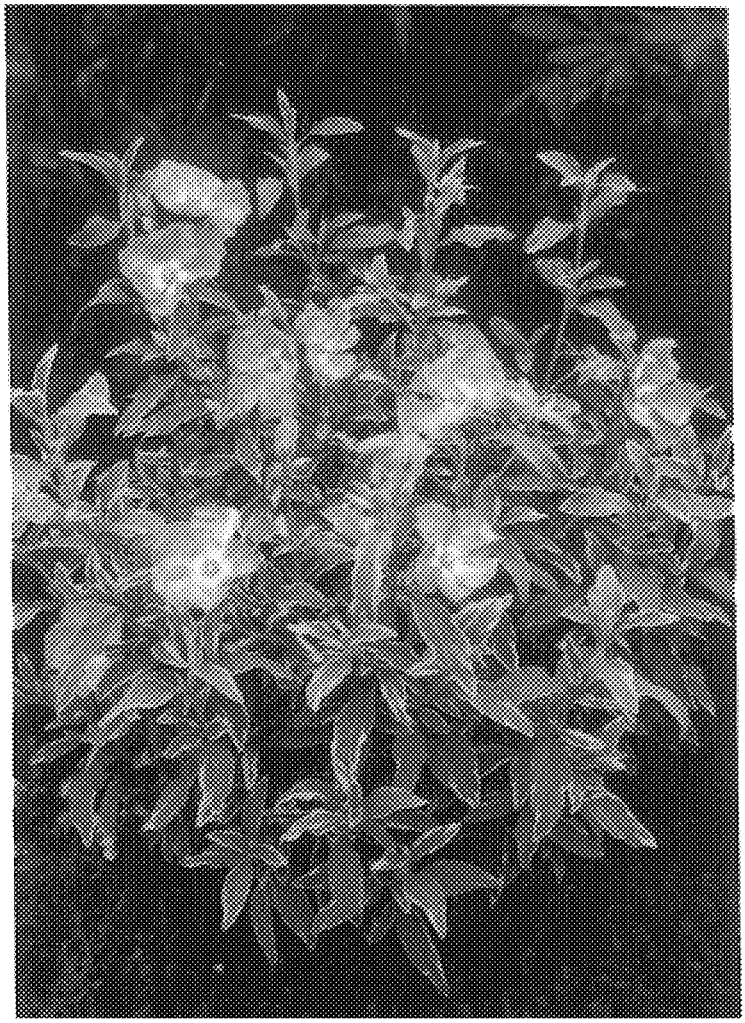

UNITED STATES PATENT AND TRADEMARK OFFICE

CERTIFICATE OF CORRECTION

PATENT NO. : Plant 10,794
DATED : February 16, 1999
INVENTOR(S) : John Hedger

It is certified that error appears in the above-identified patent and that said Letters Patent is hereby corrected as shown below:

Column 1, line 19, replace "progagations" with -- propagations --.
Column 1, line 24, before "variety" insert -- new --.
Column 2, line 14, replace "about 5.." with -- about 5. --.
Column 2, line 47, replace "Ellipitic" with -- Elliptic --.

Signed and Sealed this

Sixth Day of June, 2000

*Attest:*

*Attesting Officer*

Q. TODD DICKINSON

*Director of Patents and Trademarks*